United States Patent [19]

Mengel et al.

[11] Patent Number: 4,523,945
[45] Date of Patent: Jun. 18, 1985

[54] 2-AMINO-6-(CYCLOPROPYLMETHYL-AMINO)-PYRIMIDINES USEFUL AS HERBICIDES AND MICROBICIDES

[75] Inventors: Rudolf Mengel; Ludwig Schröder, both of Ingelheim; Werner Stransky, Gau-Algesheim; Gerbert Linden, Ingelheim; Gerhart Schneider, Mühltal; Sigmund Lust, Darmstadt, all of Fed. Rep. of Germany

[73] Assignee: Celamerck, Gesellschaft mit beschränkter Haftung & Co. KG, Ingelheim am Rein, Fed. Rep. of Germany

[21] Appl. No.: 580,079

[22] Filed: Feb. 14, 1984

[30] Foreign Application Priority Data

Feb. 18, 1983 [DE]  Fed. Rep. of Germany ....... 3305524

[51] Int. Cl.³ .................. A01N 43/48; C07D 239/02; A61K 31/505
[52] U.S. Cl. ........................................ 71/92; 544/321; 544/323; 514/275
[58] Field of Search .................... 544/323, 321; 71/92; 424/251

[56]  References Cited
PUBLICATIONS

Chem. Abstract, vol. 98, (1983):89385y, Francois et al.

Primary Examiner—Donald G. Daus
Assistant Examiner—Cecilia Shen
Attorney, Agent, or Firm—Hammond & Littell, Weissenberg & Dippert

[57]  ABSTRACT

Compounds of the formula

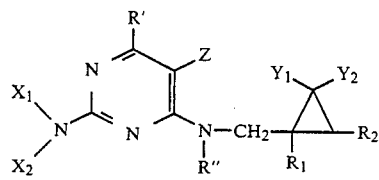

wherein $R'$, $R''$, $R_1$, $R_2$, $X_1$, $X_2$, $Y_1$, $Y_2$ and $Z$ are variable substituents of different types. The compounds are useful as herbicides and microbicides.

9 Claims, No Drawings

2-AMINO-6-(CYCLOPROPYLMETHYL-AMINO)-PYRIMIDINES USEFUL AS HERBICIDES AND MICROBICIDES

This invention relates to novel pyrimidine derivatives, to methods of preparing these compounds, to biocidal compositions containing them as active ingredients, and to methods of using them as herbicides and microbicides.

More particularly, the present invention relates to a novel class of compounds represented by the formula

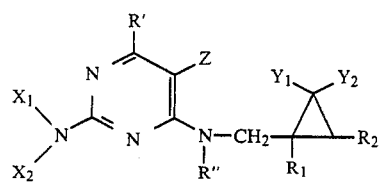 (I)

wherein
R' is hydrogen, halogen, straight or branched alkyl of 1 to 4 carbon atoms, lower alkoxy, methylthio or di(lower alkyl)amino;
R" is hydrogen, straight or branched alkyl of 1 to 4 carbon atoms or

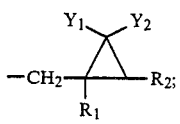

$R_1$ and $R_2$, which may be identical to or different from each other, are each hydrogen or straight or branched alkyl of 1 to 4 carbon atoms which may optionally be interrupted by —O— or —N—, especially hydrogen or methyl;
$X_1$ is hydrogen, straight or branched alkyl of 1 to 6 carbon atoms, alkenyl of 2 to 5 carbon atoms or $R_6$—$SO_2$—, especially hydrogen, methyl, ethyl, n-propyl or n-butyl;
$X_2$ is hydrogen; straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogen which may be identical to or different from each other; mono- or polysubstituted benzyl, where the substituents are one alkyl of 1 to 4 carbon atoms and/or 1 to 3 halogens which may be identical to or different from each other;

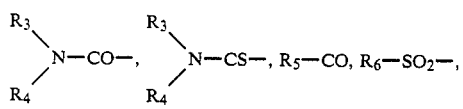

$R_6$—$SO_2$—NH—, $R_6$—$SO_2$—NH—CO—, $R_7$—O—CO—,

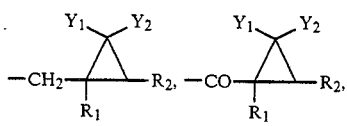

—CH=C(CN)$_2$ or —CH=N—CN; or $X_1$ and $X_2$ together with each other are $(CH_3)_2N$—CH=;

$R_3$ and $R_4$, which may be identical to or different from each other, are each hydrogen or straight or branched alkyl of 1 to 4 carbon atoms;
$R_5$ is hydrogen, straight or branched alkyl of 1 to 6 carbon atoms; mono- di- or trihalo-substituted methyl; phenyl; or mono- or polysubstituted phenyl, where the substituents are one methyl and/or 1 to 3 halogens which may be identical to or different from each other;
$R_6$ is straight or branched alkyl of 1 to 6 carbon atoms; trifluoromethyl; phenyl; benzyl; mono- or polysubstituted phenyl, where the substituents are one methyl, lower alkoxy or —COOR$_7$ and/or 1 to 3 halogens which may be identical to or different from each other; or mono- or polysubstituted benzyl, where the substituents are one methyl, lower alkoxy or COOR$_7$ and/or 1 to 3 halogens which may be identical to or different from each other; and
$R_7$ is straight or branched alkyl of 1 to 6 carbon atoms;
$Y_1$ is hydrogen, chlorine or bromine;
$Y_2$ is chlorine or bromine; and
Z is hydrogen, halogen or methylthio, preferably hydrogen or methylthio, and especially hydrogen.

Preferred are those compounds of the formula I wherein $X_2$ is hydrogen; straight or branched alkyl of 1 to 6 carbon atoms; alkenyl of 2 to 5 carbon atoms; phenyl; benzyl; formyl; acetyl; $CH_3$—O—CO—; $CF_3SO_2$—; mono- or polysubstituted phenyl, where the substituents are one alkyl of 1 to 4 carbon atoms and/or 1 to 3 halogens which may be identical to or different from each other; or mono- or polysubstituted benzyl, where the substituents are one alkyl of 1 to 4 carbon atoms and/or 1 to 3 halogens which may be identical to or different from each other; especially hydrogen, straight or branched alkyl of 1 to 6 carbon atoms or the above phenyl or benzyl radicals.

A preferred subgenus is constituted by those compounds of the formula I wherein
R' and R" have the meanings previously defined;
$R_1$ and $R_2$, which may be identical to or different from each other, are each hydrogen or methyl;
$X_1$ is hydrogen;
$X_2$ is hydrogen; straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogens which may be identical to or different from each other; mono- or polysubstituted benzyl, where the substituents are one alkyl of 1 to 4 carbon atoms and/or 1 to 3 halogens which may be identical to or different from each other; formyl; acetyl; $CH_3O$—CO—; or $CF_3SO_2$—; and
Z is hydrogen or methylthio.

An especially preferred subgenus is constituted by those compounds of the formula I wherein
$R_1$ is halogen;
R" is straight or branched alkyl of 1 to 4 carbon atoms;
$R_1$ and $R_2$, which may be identical to or different from each other, are each hydrogen or methyl;
$X_1$ is hydrogen;

$X_2$ is hydrogen, straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogens which may be identical to or different from each other; or mono- or polysubstituted benzyl, where the substituents are one alkyl of 1 to 4 carbon atoms and or 1 to 3 halogens which may be identical to or different from each other.

The term "halogen" is intended to mean fluorine, chlorine or bromine.

The term "lower alkyl" is intended to mean methyl, ethyl, n-propyl, isopropyl, n-butyl, sec-butyl, tert-butyl, n-pentyl, isoamyl or n-hexyl, for example.

The term "lower alkoxy" is intended to include methoxy, ethoxy, propoxy or the like, The term "alkenyl" is meant to include vinyl, propenyl-(1), allyl, butenyl-(1), butenyl-(2), butenyl-(3) or pentenyl-(2), for example.

The compounds embraced by formula I may be prepared by the following methods:

Method A

By reacting a pyrimidine derivative of the formula

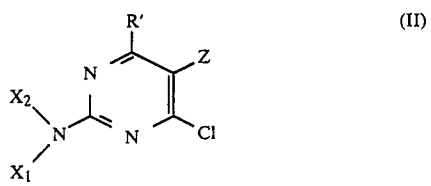

wherein R', $X_1$, $X_2$ and Z have the meanings previously defined, with an amine of the formula

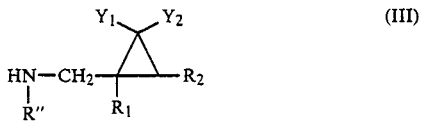

wherein R'', $R_1$, $R_2$, $Y_1$ and $Y_2$ have the meanings previously defined.

Method B

By reacting a pyrimidine derivative of the formula

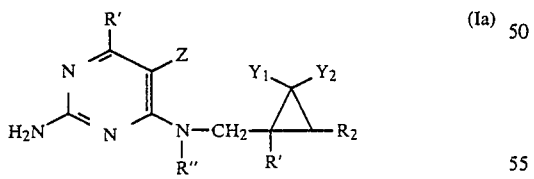

wherein R', R'', $R_1$, $R_2$, $Y_1$ and $Y_2$ have the meanings previously defined, with a suitable acylating agent such as acetic acid-formic acid anhydride, acetyl chloride or an isocyanate.

An end product of the formula I wherein Z is hydrogen obtained by method A or B may, if desired, be converted into the corresponding compound wherein Z is halogen by means of conventional halogenation methods.

The reaction in methods A and B is advantageously carried out in an inert solvent such as ethanol, toluene, methylene chloride or acetonitrile. The reaction in method A is preferably carried out in the presence of an acid-binding agent such as triethylamine. In either case, the reaction may be performed at room temperature or at elevated temperature up to and including the boiling point of the reaction mixture, and the reaction product may be purified by conventional methods. Depending upon the reactivity of the starting compounds, it is recommended to work in an anhydrous medium.

The subsequent exchange of the hydrogen atom in the 5-position of the pyrimidine ring for a halogen atom is advantageously performed at a temperature between −20° and +30° C. in a halogenated lower hydrocarbon such as carbon tetrachloride or methylene chloride.

The starting compounds of the formula II are disclosed in the literature or may be prepared by methods described in the literature.

The cyclopropylmethyl-amines of the formula III may be prepared by conventional methods, for instance by means of the Gabriel Synthesis. Starting compounds of the formula III wherein $Y_1$ and $Y_2$ are hydrogen may be obtained by reduction of the corresponding dihalo compounds.

The following examples illustrate the present invention and will enable others skilled in the art to understand it more completely. It should be understood, however, that the invention is not limited solely to the particular examples given below.

EXAMPLE 1

2-Amino-4-chloro-6-{[(2,2-dichloro-cyclopropyl)-methyl]amino}pyrimidine

A mixture consisting of 38.8 gm (0.24 mol) of 2-amino-4,6-dichloro-pyrimidine, 300 ml of ethanol, 33.1 gm (0.24 mol) of (2,2-dichloro-cyclopropylmethyl)amine and 36 ml (0.26 mol) of triethylamine was refluxed for six hours while stirring. Thereafter, the solvent was distilled off, the oily residue was stirred with about 300 ml of acetone, and the precipitated triethylamine hydrochloride was suction-filtered off. The acetone was distilled out of the filtrate in vacuo, and the residue was admixed with 500 ml of diisopropyl ether and 100 ml of water. The organic phase was separated and again washed with water, dried with magnesium sulfate, decolorized and evaporated. The residue was triturated with gasoline (b.p. 40°–60° C.) to yield the title compound as colorless crystals.

Yield: 53.3 gm (84.4% of theory).

M.p.: 78°–79° C.

EXAMPLE 2

2-Formylamino-4-chloro-6-{[(2,2-dichloro-cyclopropyl)-methyl]amino}pyrimidine

A solution of 2.7 g (0.01 mol) of 2-amino-4-chloro-6-{[(2,2-dichloro-cyclopropyl)methyl]amino}pyrimidine in 300 ml of acetonitrile was added dropwise, while stirring, at room temperature over a period of 15 minutes to a solution of 0.9 gm (0.012 mol) of acetic acid-formic acid anhydride in 5 ml of acetonitrile. After stirring the mixture for about 30 hours at room temperature the solvent was distilled off in vacuo, and the residue was treated twice by dissolving it in about 30 ml of toluene and then distilling the toluene off again. The raw product was purified by column chromatography (150 gm silica gel; eluant: Diisopropyl ether/ethyl acetate 9:1), yielding the title compound as white crystals.

Yield: 1.0 gm (33.9% of theory).

M.p.: 152° C.

TABLE I

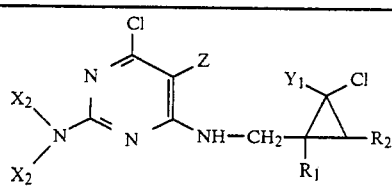

| Example No. | R₁ | R₂ | X₁ | X₂ | Y₁ | Z | M.p. |
|---|---|---|---|---|---|---|---|
| 3 | H | H | H | H | Cl | H | 78-79° C. |
| 4 | H | H | H | H | Cl | Cl | 139° C. |
| 5 | H | H | H | H | Cl | Br | |
| 6* | H | H | H | H | Cl | —SCH₃ | |
| 7 | H | H | H | HCO— | Cl | H | 152° C. |
| 8 | H | H | H | HCO— | Cl | Cl | |
| 9 | H | H | H | HCO— | Cl | Br | |
| 10* | H | H | H | HCO— | Cl | —SCH₃ | |
| 11 | H | H | H | CH₃CO— | Cl | Cl | |
| 12 | H | H | H | CH₃CO— | Cl | Br | |
| 13* | H | H | H | CH₃CO— | Cl | —SCH₃ | |
| 14 | H | H | H | ClCH₂CO— | Cl | Cl | |
| 15 | H | H | H | ClCH₂CO— | Cl | Br | |
| 16 | H | H | H | ClCH₂CO— | Cl | —SCH₃ | |
| 17 | H | H | H | CF₃CO— | Cl | Cl | |
| 18 | H | H | H | CF₃CO— | Cl | Br | |
| 19* | H | H | H | CF₃CO— | Cl | —SCH₃ | |
| 20 | H | H | H | (CH₃)₂CHCO— | Cl | Cl | |
| 21 | H | H | H | (CH₃)₂CHCO— | Cl | Br | |
| 22 | H | H | H | (CH₃)₂CHCO— | Cl | —SCH₃ | |
| 23 | H | H | H | (CH₃)₃CCO— | Cl | H | Oil |
| 24 | H | H | H | (CH₃)₃CCO— | Cl | Cl | |
| 25 | H | H | H | (CH₃)₃CCO— | Cl | Br | |
| 26 | H | H | H | CH₃CH₂CO— | Cl | H | |
| 27 | H | H | H | CH₃CH₂CO— | Cl | Cl | |
| 28 | H | H | H | CH₃CH₂CO— | Cl | Br | |
| 29 | H | H | H | CH₃CH₂CH₂CO— | Cl | H | |
| 30 | H | H | H | CH₃CH₂CH₂CO— | Cl | Cl | |
| 31 | H | H | H | CH₃CH₂CH₂CO— | Cl | Br | |
| 32 | H | H | H | n-Bu—CO— | Cl | H | |
| 33 | H | H | H | n-Bu—CO— | Cl | Cl | |
| 34 | H | H | H | —CH₃ | Cl | Cl | |
| 35 | H | H | H | —CH₃ | Cl | H | 105° C. |
| 36* | H | H | H | —CH₃ | Cl | —SCH₃ | |
| 37 | H | H | H | —C₂H₅ | Cl | H | 88° C. |
| 38 | H | H | H | (CH₃)₂CH | Cl | H | |
| 39 | H | H | —CH₃ | —CH₃ | Cl | H | |
| 40 | H | H | —CH₃ | —CH₃ | Cl | Cl | |
| 41* | H | H | —CH₃ | —CH₃ | Cl | —SCH₃ | |
| 42 | —CH₃ | H | H | H | Cl | H | |
| 43 | —CH₃ | H | H | H | Cl | Cl | |
| 44* | —CH₃ | H | H | H | Cl | —SCH₃ | |
| 45 | H | H | H | CH₃CO— | Cl | H | |
| 46 | —CH₃ | H | H | HCO— | Cl | H | |
| 47 | —CH₃ | H | H | CH₃CO— | Cl | H | |
| 48 | —CH₃ | H | H | ClCH₂CO— | Cl | H | |
| 49 | —CH₃ | H | H | CF₃CO— | Cl | H | |
| 50 | —CH₃ | H | H | (CH₃)₂CHCO— | Cl | H | |
| 51 | —CH₃ | H | H | (CH₃)₃CCO— | Cl | H | |
| 52 | —CH₃ | H | H | CH₃CH₂CO— | Cl | H | |
| 53 | —CH₃ | H | H | CH₃CH₂CH₂CO— | Cl | H | |
| 54 | —CH₃ | H | H | n-Bu—CO— | Cl | H | |
| 55 | H | —CH₃ | H | H | Cl | H | |
| 56 | H | —CH₃ | H | H | Cl | Cl | |
| 57* | H | —CH₃ | H | H | Cl | —SCH₃ | |
| 58 | H | —CH₃ | H | HCO— | Cl | H | |
| 59 | H | —CH₃ | H | CH₃CO— | Cl | H | |
| 60 | H | —CH₃ | H | CF₃CO— | Cl | H | |
| 61 | H | —CH₃ | H | ClCH₂CO— | Cl | H | |
| 62 | H | —CH₃ | H | —CH₃ | Cl | H | |
| 63 | H | —CH₃ | —CH₃ | —CH₃ | Cl | H | |
| 64 | —CH₃ | —CH₃ | H | H | Cl | H | |
| 65 | —CH₃ | —CH₃ | H | H | Cl | Cl | |
| 66* | —CH₃ | —CH₃ | H | H | Cl | —SCH₃ | |
| 67 | —CH₃ | —CH₃ | H | HCO— | Cl | H | |
| 68 | —CH₃ | —CH₃ | H | CH₃CO— | Cl | H | |
| 69 | —CH₃ | —CH₃ | H | —CH₃ | Cl | H | |
| 70 | —CH₃ | —CH₃ | —CH₃ | —CH₃ | Cl | H | |
| 71 | —CH₃ | —CH₃ | —CH₃ | —CH₃ | Cl | Cl | |
| 72* | —CH₃ | —CH₃ | —CH₃ | —CH₃ | Cl | —SCH₃ | |

TABLE I-continued $$\underset{\underset{X_2}{X_2}}{\overset{Cl}{\underset{N}{\bigg\langle}}}\text{N}\overset{Z}{\underset{N}{\bigg\rangle}}\text{NH-CH}_2\overset{Y_1}{\underset{R_1}{\bigg\langle}}\overset{Cl}{\underset{R_2}{\bigg\rangle}}$$

| Example No. | R₁ | R₂ | X₁ | X₂ | Y₁ | Z | M.p. |
|---|---|---|---|---|---|---|---|
| 73 | H | H | H | Cl₂C₃H₃(CH₂)— (gem-dichlorocyclopropylmethyl) | Cl | H | |
| 74* | H | H | H | Cl₂C₃H₃(CH₂)— | Cl | —SCH₃ | 96° C. |
| 75 | H | H | H | Cl₂(CH₃)C₃H₂(CH₂)— | Cl | H | 98° C. |
| 76 | H | —CH₃ | H | Cl₂(CH₃)C₃H₂(CH₂)— | Cl | —SCH₃ | |
| 77 | H | H | H | Cl₂C₃H₂(CH₃)(CH₂)— | Cl | H | |
| 78 | —CH₃ | H | H | Cl₂C₃H₃(CH₂)— | Cl | —SCH₃ | |
| 79 | H | —CH₂OCH₃ | H | H | Cl | H | |
| 80 | H | —CH₂CH₂OCH₃ | H | H | Cl | H | |
| 81 | H | —CH₂N(CH₃)₂ | H | H | Cl | H | |
| 82 | H | H | H | 2-Cl-C₆H₄-SO₂NHCO— | Cl | H | 215° C. |
| 83 | H | H | H | 2-OCH₃-C₆H₄-SO₂NHCO— | Cl | H | 174° C. |
| 84 | H | H | H | H | H | H | oil |
| 85* | H | H | H | H | H | —SCH₃ | |
| 86 | H | H | H | H | H | Cl | |
| 87 | H | H | H | HCO— | H | H | |
| 88 | H | H | H | HCO— | H | Cl | |
| 89 | H | H | H | CF₃CO— | H | H | |
| 90 | H | H | H | CF₃CO— | H | Cl | |
| 91* | —CH₃ | H | H | H | H | H | |
| 92 | —CH₃ | H | H | H | H | Cl | |
| 93 | —CH₃ | H | H | H | H | —SCH₃ | |
| 94 | —CH₃ | H | H | HCO— | H | H | |
| 95 | —CH₃ | H | H | HCO— | H | Cl | |
| 96* | —CH₃ | H | H | HCO— | H | —SCH₃ | |
| 97 | —CH₃ | H | H | CF₃CO— | H | H | |
| 98 | —CH₃ | H | H | CF₃CO— | H | Cl | |
| 99* | —CH₃ | H | H | CF₃CO— | H | —SCH₃ | |
| 100 | H | —CH₃ | H | H | H | H | |
| 101 | H | —CH₃ | H | HCO— | H | Cl | |
| 102 | H | —CH₃ | H | CF₃CO— | H | Cl | |
| 103 | H | H | H | H,Cl-C₃H₂(CH₂)— (monochlorocyclopropylmethyl) | H | H | |

TABLE I-continued

[Structure: chloropyrimidine with guanidine group N(X2)(X2), substituent Z, and NH-CH2-cyclopropyl group with R1, R2, Y1, Cl]

| Example No. | R1 | R2 | X1 | X2 | Y1 | Z | M.p. |
|---|---|---|---|---|---|---|---|
| 104 | H | H | H | H₂C(Cl)–cyclopropyl–CH2– | H | Cl | |
| 105* | H | H | H | H₂C(Cl)–cyclopropyl–CH2– | H | —SCH3 | |
| 106 | H | H | H | CF3CO— | Cl | H | oil |
| 107 | H | H | H | (CH3)CHCO— | Cl | H | |

TABLE II

[Structure: pyrimidine with R', Z, guanidine N(X1)(X2), and N(R")-CH2-CH-CH2 cyclopropyl with Y1, Y2]

| Example No. | X2 | X1 | R' | Z | R" | Y1 | Y2 | M.p. |
|---|---|---|---|---|---|---|---|---|
| 108 | 2-Cl-C6H4-SO2NH-C(=O)- | H | —OCH3 | H | H | Cl | Cl | 195° C. |
| 109 | H | H | —OCH3 | H | H | Cl | Cl | oil |
| 110 | H | H | —CH3 | H | H | Cl | Cl | 118° C. |
| 111 | 2-Cl-C6H4-SO2NH-C(=O)- | H | —CH3 | H | H | Cl | Cl | amorphous 115° C. |
| 112 | H | H | —SCH3 | H | H | Cl | Cl | 105° C. |
| 113 | 2-COOCH3-C6H4-SO2NH-C(=O)- | H | —SCH3 | H | H | Cl | Cl | 184° C. |
| 114 | H | H | (CH3)2N— | H | H | Cl | Cl | 110° C. |
| 115 | ClCH3—C(=O)— | H | Cl | H | H | Cl | Cl | 116° C. |
| 116 | C6H5—C(=O)— | H | Cl | H | H | Cl | Cl | oil. |
| 117 | Cl2C-CH2-C(CH3)-C(=O)- (cyclopropyl) | H | Cl | H | H | Cl | Cl | oil |
| 118 | CF3SO2— | H | Cl | H | H | Cl | Cl | oil |

TABLE II-continued

Structure:
$$X_1X_2N-C(=N-)-N=C(R')-C(Z)=C(-N(R'')-CH_2-CH(-)-)... \text{ with cyclopropane } C(Y_1)(Y_2)$$

| Example No. | X₂ | X₁ | R' | Z | R'' | Y₁ | Y₂ | M.p. |
|---|---|---|---|---|---|---|---|---|
| 119 | 2,4-dichlorobenzyl-SO₂-NH-C(=O)- | H | Cl | H | H | Cl | Cl | 103° C. |
| 120 | -CH=C(CN)₂ | H | Cl | H | H | Cl | Cl | 174° C. |
| 121 | =CH-N(CH₃)₂ | H | Cl | H | H | Cl | Cl | 186° C. |
| 122 | 2-chlorobenzoyl- | H | Cl | H | H | Cl | Cl | 156° C. |
| 123 | -CH₃ | -CH₃ | Cl | H | H | Cl | Cl | 113° C. |
| 124 | H | H | Cl | H | H | Br | Br | 86° C. |
| 125 | CF₃SO₂- | CF₃SO₂- | Cl | H | H | Cl | Cl | 111° C. |
| 126 | H | H | Cl | H | H | H | H | oil |
| 127 | C₂H₅-O-C(=O)-N(H)-C(=O)- | H | Cl | H | H | Cl | Cl | 224° C. |
| 128 | CH₃SO₂- | CH₃SO₂- | Cl | H | H | Cl | Cl | 134° C. |
| 129 | CH₃NH-C(=O)- | H | Cl | H | H | Cl | Cl | 210° C. |
| 130 | -CH₃ | H | Cl | H | H | Cl | H | oil |
| 131 | H | H | Cl | H | -CH₂-cyclopropyl(Cl,Cl) | Cl | Cl | 158° C. |
| 132 | CH₂=CH-CH₂- | H | Cl | H | -CH₂-cyclopropyl(Cl,Cl) | Cl | Cl | |
| 133 | -CH₃ | -CH₃ | Cl | H | H | Cl | H | oil |
| 134 | H | H | Cl | H | -CH₃ | Cl | Cl | 126° C. |
| 135 | -C₂H₅ | H | Cl | H | -CH₃ | Cl | Cl | 89° C. |
| 136 | CH₂=CH-CH₂- | H | Cl | H | -CH₃ | Cl | Cl | |
| 137 | C₆H₅-CH₂- | H | Cl | H | H | Cl | Cl | 119° C. |

TABLE II-continued

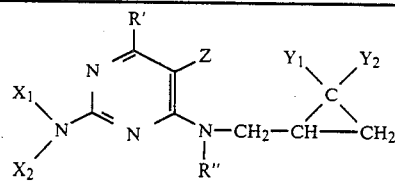

| Example No. | X2 | X1 | R' | Z | R" | Y1 | Y2 | M.p. |
|---|---|---|---|---|---|---|---|---|
| 138 | CH2=CH—CH2—CH2— | H | Cl | H | H | Cl | Cl | |
| 139 | CH3—CH2—CH=CH— | H | Cl | H | —CH3 | Cl | H | |
| 140 | ⟨phenyl⟩—CH2— | H | Cl | H | H | Cl | H | 106° C. |
| 141 | —C2H5 | H | Cl | H | —C2H5 | Cl | Cl | 109° C. |
| 142 | H | H | Cl | H | H | Cl | Cl | 123° C. |
| 143 | CH3—CH=CH— | H | Cl | H | H | Cl | H | |
| 144 | ⟨phenyl⟩— | H | Cl | H | H | Cl | Cl | 101° C. |
| 145 | ⟨phenyl⟩— | H | Cl | H | —C2H5 | Cl | Cl | oil |
| 146 | ⟨phenyl⟩— | H | Cl | H | —CH3 | Cl | Cl | 123° C. |
| 147 | H | H | (CH3)2N— | H | —CH3 | Cl | Cl | 82° C. |
| 148 | H | H | —OCH3 | H | —CH3 | Cl | Cl | 91° C. |
| 149 | CH3—CH=CH—CH2— | H | —CH3 | H | H | Cl | Cl | |

The compounds of the present invention, that is, those embraced by formula I and their salts have useful properties. More particularly, they exhibit herbicidal and microbicidal activities. They can be used for pre-emergence and especially for post-emergence treatment against numerous weeds and undesirable grasses such as

| | |
|---|---|
| Amaranthus retroflexus | Sida spinosa |
| Abutilon theophrasti | Sinapis arvensis |
| Bidens pilosa | Stellaria media |
| Cassia tora | Veronica persicaria |
| Centaurea cyanus | Veronica hederaefolia |
| Datura stramonium | Xanthium pensylvanicum |
| Desmodium tortuosum | Alopecurus myosuroides |
| Galium aparine | Avena fatua |
| Ipomoea purpurea | Echinochloa crus-galli |
| Ipomoea hederacea | Echinochloa colonum |
| Ipomea aconitifolia | Eleusine indica |
| Lamium purpurea | Digitaria sanguinalis |
| Lamium amplexicaule | Cynodon dactylon |
| Lapsana communis | Leptochloa filiformis |
| Portulaca oleracea | Sorghum halepense |
| | Setaria viridis |

In addition to being suitable for use as total herbicides at high concentrations, the good selectivity of the compounds enables them to be used at lower concentrations to combat weeds and wild plants in numerous crops; they may be used, for example, in wheat, barley and other types of cereals, in corn, millet, rice, sugar cane, soy beans, cotton, sugar beets, potatoes, rape, etc.

For use, the compounds of the formula I are processed with conventional excipients and/or carriers in known manner to produce conventional formulations, such as emulsion concentrates or wettable powders, wherein the content of active ingredient is between 10 and 95% by weight and which can be diluted with water to give the desired concentration of active substance for application. However, it is also possible to produce compositions in the form of dusting powders or granulates which can be used undiluted. In these compositions the content of active substance is between 0.1 and 10% by weight, preferably between 0.3 and 3% by weight.

Suitable carriers include, for example, kaolin, talc, chalk, aluminum silicates, powdered cereals, cellulose powder, sawdust, etc. Suitable dispersants include condensation products of naphthalene or naphthalenesulfonic acids with phenyl and formaldehyde, salts of ligninsulfonic acid, salts of sulfated hexa-, hepta- and octadecanols, etc. Silicones are suitable for use as anti-foaming agents. Water, alcohols, aromatic hydrocarbons, dimethylsulfoxide, mineral oils and vegetable oils may be used as solvents.

The following examples illustrate a few agricultural compositions comprising a compound of the present invention as an active ingredient and represent the best modes contemplated of using the invention. The percentages are percent by weight.

EXAMPLE 150

Emulsion concentrate

10% of a compound of formula I
40% of vegetable oil
10% of nonylphenolpolyglycol ether
40% of cyclohexanone

EXAMPLE 151

Suspension powder

25% of a compound of formula I
55% of kaolin
10% of colloidal silicic acid
9% of calcium lignin sulfonate
1% of sodium tetrapropylene benzenesulfonate

EXAMPLE 152

Suspension powder

95% of a compound of formula I
4% of calcium lignin sulfonate
1% of sodium tetrapropylene benzenesulfonate

EXAMPLE 153

Dusting powder 0.3% of a compound of formula I
1.0% of methyl cellulose
98.7% of talc Spraying liquors which generally contain between 0.005 and 0.5% of active ingredient are prepared from the concentrates of Examples 150 to 153 by mixing with water.

Surprisingly, the compounds of the present invention have an extremely favorable microbicidal spectrum against phytopathogenic fungi and bacteria. They have curative, preventive and systemic properties and can be used to protect cultivated plants. The active substances according to the invention may be used with particular advantage against the following classes of phytopathogenic fungi: Ascomycetae, Basidiomycetae, Fungi imperfecti and Phytomycetae. The following types of plants are suitable for treatment: cereals, kernel, stone and berry fruit, pulses, oil crops, cucumbers, fibrous plants, citrus fruits, vegetables, laurels, corn, tobacco, nuts, coffee, sugar canes, tea, grape vines, hops, bananas and natural rubber crops and Compositae.

Active substances of the formula I may be applied simultaneously or one after another with other active substances to the surface of plants which are to be treated; these other active substances may be preparations which affect plant growth or they may be plant protecting agents.

For microbicidal use, the compounds according to the invention and optionally also the salts thereof may be processed in the usual way with excipients and/or carriers to form conventional pesticidal agents, e.g. solutions, solution or emulsion concentrates, suspension powders, dusting powders or emulsions. If required, the concentrates are diluted with water before use so as to produce spray liquors with a content of active substance of between about 0.005 and 1% by weight. When they are used as low-volume or ultra-low-volume preparations, the content of active substance may also be considerably higher (up to 20 or 50% by weight, respectively).

Preferred methods of application are leaf application, soil application and coating of the seeds.

The following are examples of compositions which are suitable for microbicidal use.

EXAMPLE 154

Wettable powder 20 parts by weight of a compound of formula I
20 parts by weight of kaolin
5 parts by weight of sodium sulfate
2 parts by weight of prepared chalk
9 parts by weight of calcium lignin sulfonate (dispersant)
1 part by weight of diisobutylnaphthalene sodium sulfonate (wetting agent)
43 parts by weight of siliceous chalk The mixture of ingredients is ground and, for use, the composition is suspended in a quantity of water such that the concentration of active substance is between about 0.005 and 0.5% by weight.

EXAMPLE 155

Emulsion concentrate 15 parts by weight of a compound of formula I
10 parts by weight of the triethylamine salt of dodecylbenzenesulfonic acid
75 parts by weight of dimethylformamide The amount of active ingredient in the illustrative composition examples may be varied to achieve the concentration ranges set forth above, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

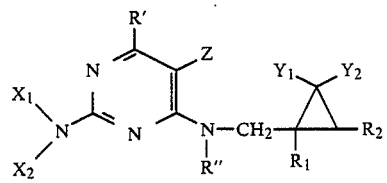

wherein
  R' is hydrogen, halogen, straight or branched alkyl of 1 to 4 carbon atoms, alkoxy of 1 to 3 carbon atoms, methylthio or di(alkyl of 1 to 6 carbon atoms)amino;
  R" is hydrogen, straight or branched alkyl of 1 to 4 carbon atoms or

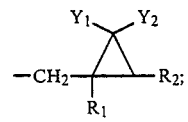

$R_1$ and $R_2$ are each hydrogen or straight or branched alkyl of 1 to 4 carbon atoms which may optionally be interrupted by —O— or —N—;
  $X_1$ is hydrogen, straight or branched alkyl of 1 to 6 carbon atoms, alkenyl of 2 to 5 carbon atoms or $R_6$—$SO_2$—;
  $X_2$ is hydrogen; straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogens which may be identical to or different from each other; mono- or polysubstituted benzyl, where the substituents are one alkyl of 1 to 4 carbon atoms and/or 1 to 3 halogens which may be identical to or different from each other;

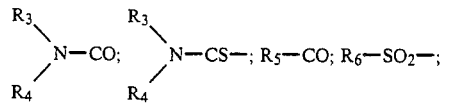

$R_6-SO_2-NH$; $R_6-SO_2-NH-CO-$; $R_7-O-CO$;

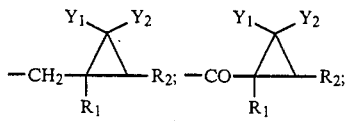

$-CH=C(CN)_2$; or $-CH=N-CN$; or $X_1$ and $X_2$ together with each other are $(CH_3)_2N-CH=$;

$R_3$ and $R_4$ are each hydrogen or straight or branched alkyl of 1 to 4 carbon atoms;

$R_5$ is hydrogen, straight or branched alkyl of 1 to 6 carbon atoms; mono-, di- or trihalo-substituted methyl; phenyl; or mono- or polysubstituted phenyl, where the substituents are one methyl and/or 1 to 3 halogens which may be identical to or different from each other;

$R_6$ is straight or branched alkyl of 1 to 6 carbon atoms; trifluoromethyl; phenyl; benzyl; mono- or polysubstituted phenyl, where the substituents are one methyl, alkoxy of 1 to 3 carbon atoms or $-COOR_7$ and/or 1 to 3 halogens which may be identical to or different from each other; or mono- or polysubstituted benzyl, where the substituents are one methyl, alkoxy of 1 to 3 carbon atoms or $COOR_7$ and/or 1 to 3 halogens which may be identical to or different from each other;

$R_7$ is straight or branched alkyl of 1 to 6 carbon atoms;

$Y_1$ is hydrogen, chlorine or bromine;

$Y_2$ is chlorine or bromine; and $Z$ is hydrogen, halogen or methylthio; or a salt thereof.

2. A compound of claim 1,
where
$R'$ and $R''$ have the meanings defined in claim 1;
$R_1$ and $R_2$ are each hydrogen or methyl;
$X_1$ is hydrogen;
$X_2$ is hydrogen; straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogens which may be identical to or different from each other; mono- or polysubstituted benzyl, where the substituents are one alkyl of 1 to 4 carbon atoms and/or 1 to 3 halogens which may be identical to or different from each other; formyl; acetyl; $CH_3O-CO-$; or $CF_3SO_2-$; and $Z$ is hydrogen or methylthio; or a salt thereof.

3. A compound of claim 1,
where
$R_1$ is hydrogen;
$R''$ is straight or branched alkyl of 1 to 4 carbon atoms;
$R_1$ and $R_2$ are each hydrogen or methyl;
$X_1$ is hydrogen;
$X_2$ is hydrogen, straight or branched alkyl of 1 to 6 carbon atoms; alkenyl of 2 to 5 carbon atoms; phenyl; benzyl; mono- or polysubstituted phenyl, where the substituents are one alkyl of 1 to 4 carbon atoms and/or 1 to 3 halogens which may be identical to or different from each other; or mono- or polysubstituted benzyl, where the substituents are one alkyl of 1 to 4 carbon atoms and/or 1 to 3 halogens which may be identical to or different from each other.

4. The compound of claim 1 which is 2-amino-4-chloro-6-{[(2,3-dichlorocyclopropyl)methyl]amino} pyrimidine.

5. The compound of claim 1 which is 2-formylamino-4-chloro-6-{[2,2-dichlorocyclopropyl)methyl]-amino} pyrimidine.

6. An herbicidal or microbicidal composition consisting essentially of an inert carrier and an effective herbicidal or microbicidal amount of a compound of claim 1.

7. The method of eradicating undesirable plants which comprises contacting said plants or seeds thereof with an effective herbicidal amount of a compound of claim 1.

8. The method of killing phytopathogenic microorganisms on useful plants, which comprises contacting said microorganisms with an effective microbicidal amount of a compound of claim 1.

9. A compound of claim 1, where $R'$, $R''$, $R_1$, $R_2$, $R_3$, $R_4$, $R_5$, $R_6$, $R_7$, $Y_1$, $Y_2$ and
$Z$ have the meanings defined in claim 1,
$X_1$ is hydrogen, and
$X_2$ is straight or branched alkyl of 1 to 6 carbon atoms.

* * * * *

UNITED STATES PATENT AND TRADEMARK OFFICE
CERTIFICATE OF CORRECTION

PATENT NO. : 4,523,945
DATED : June 18, 1985
INVENTOR(S) : RUDOLF MENGEL ET AL.

It is certified that error appears in the above-identified patent and that said Letters Patent is hereby corrected as shown below:

Col. 9, before Table II, the following paragraph should be inserted:

-- * Due to the method of preparation of the starting compounds, these end products are mixtures of the 2-(optionally substituted amino)-4-chloro- and 2-chloro-4-(optionally substituted amino)-pyrimidine derivatives. --

Col. 9, Ex. 115 - "ClCH$_3$" should read -- ClCH$_2$ --.

Col. 18, line 32 - "6-{[2,2" should read -- 6-{[(2,2 --.

Signed and Sealed this

Thirty-first Day of December 1985

[SEAL]

Attest:

DONALD J. QUIGG

Attesting Officer

Commissioner of Patents and Trademarks